United States Patent [19]
Poncet

[11] Patent Number: 6,113,610
[45] Date of Patent: Sep. 5, 2000

[54] DEVICE AND METHOD FOR SUTURING WOUND

[75] Inventor: Philippe Poncet, Fremont, Calif.

[73] Assignee: Medtronic, Inc., Minneapolis, Minn.

[21] Appl. No.: 09/166,619

[22] Filed: Oct. 5, 1998

Related U.S. Application Data

[62] Division of application No. 08/858,782, May 19, 1997, Pat. No. 5,817,108, which is a continuation of application No. 08/474,613, Jun. 7, 1995, abandoned.

[51] Int. Cl.[7] .................................................. A61B 17/00
[52] U.S. Cl. ........................... 606/139; 606/144; 128/898
[58] Field of Search ..................... 606/139, 144, 606/148, 147, 185; 128/898

[56] References Cited

U.S. PATENT DOCUMENTS

| 4,665,906 | 5/1987 | Jervis | 128/92 |
|---|---|---|---|
| 5,002,563 | 3/1991 | Pyka et al. | 606/222 |
| 5,219,358 | 6/1993 | Bendel et al. | 606/222 |
| 5,250,055 | 10/1993 | Moore et al. | 606/148 |
| 5,304,184 | 4/1994 | Hathaway et al. | 606/144 |
| 5,320,632 | 6/1994 | Heidmueller | 606/144 |
| 5,364,408 | 11/1994 | Gordon | 606/144 |
| 5,368,601 | 11/1994 | Sauer et al. | 606/144 |
| 5,374,275 | 12/1994 | Bradley et al. | 606/144 |
| 5,383,882 | 1/1995 | Buess et al. | 606/157 |
| 5,403,328 | 4/1995 | Shallman | 606/144 |
| 5,403,329 | 4/1995 | Hinchliffe | 606/147 |
| 5,417,699 | 5/1995 | Klein et al. | 606/144 |
| 5,462,561 | 10/1995 | Voda | 606/144 |
| 5,468,251 | 11/1995 | Buelna | 606/223 |
| 5,470,338 | 11/1995 | Whitfield et al. | 606/144 |
| 5,474,568 | 12/1995 | Scott | 606/144 |
| 5,478,353 | 12/1995 | Yoon | 606/213 |
| 5,486,183 | 1/1996 | Middleman et al. | 606/127 |
| 5,496,332 | 3/1996 | Sierra et al. | 606/139 |
| 5,507,744 | 4/1996 | Tay et al. | 606/50 |
| 5,527,321 | 6/1996 | Hinchliffe | 606/144 |
| 5,527,322 | 6/1996 | Klein et al. | 606/144 |
| 5,540,704 | 7/1996 | Gordon et al. | 606/144 |
| 5,540,705 | 7/1996 | Meade et al. | 606/145 |
| 5,578,044 | 11/1996 | Gordon et al. | 606/139 |
| 5,591,179 | 1/1997 | Edelstein | 606/144 |
| 5,601,572 | 2/1997 | Middleman et al. | 606/139 |
| 5,755,727 | 5/1998 | Kontos | 606/139 |
| 5,860,991 | 1/1999 | Klein et al. | 606/139 |

FOREIGN PATENT DOCUMENTS 0634141  1/1995  European Pat. Off. ........ A61B 17/04

Primary Examiner—Michael Buiz
Assistant Examiner—Kevin Truong
Attorney, Agent, or Firm—Sheldon & Mak

[57] ABSTRACT

A surgical device for closing trocar incision sites and delivering sutures. The present invention is a needle assembly in which the needle is constructed of a spring-like material and initially housed within a sheath in a deformed condition. The needle can be easily exposed by sliding an actuator so as to release the constraining means and allow the needle to assume its undeformed condition. The needle assembly has few parts, allows a wide range for deflection of the needle, and the needle may be exposed with a relatively short stroke.

14 Claims, 4 Drawing Sheets

DEVICE AND METHOD FOR SUTURING WOUND

This application is a divisional of patent application Ser. No. 08/858,782, filed on May 19, 1997, now U.S. Pat. No. 5,817,108 which is a continuation of patent application Ser. No. 08/474,613, filed on Jun. 7, 1995, now abandoned.

This invention relates to a surgical instrument for closing the edges of a wound together with surgical sutures.

BACKGROUND OF THE INVENTION

Minimum invasive surgery generally includes the creation of trocar puncture wounds through the abdominal wall of a patient for insertion of a variety of surgical instruments. The structural strength of the abdominal wall is derived mostly from one or more layers of fascia disposed beneath the skin and between layers of muscle. Unless closed properly, the abdominal contents may herniate through these wounds. or body fluids can accumulate, promoting infection. Presently, surgeons attempt to close trocar puncture wounds using conventional needle drivers which are often cumbersome, making it difficult to properly close the wound.

Larger trocars (10 mm and larger) are commonly used for surgical procedures. For large trocars and to avoid potential hernias, it is desirable to utilize flexible threads, or sutures, passing through apposing tissue edges tied to hold the more deeply buried portions of the edge of the wound together. Attempts have been made to address these problems, for example, in U.S. Pat. Nos. 5,368,601 to Sauer et al; 5,374,275 to Bradley et al; and European Patent Application No. 0 634 141. However, these devices employ multiple needles, which result in a complex device which is complicated in use and expensive to manufacture.

U.S. Pat. No. 5,403,328 to Shallman describes a surgical apparatus for closing a trocar incision. The Shallman device includes a curved needle pivotally positioned within a casing. The mechanism for pivoting the needle of Shallman is somewhat cumbersome, even while deflection of the needle is limited, and requires a long stroke to manipulate the needle.

SUMMARY OF THE INVENTION

The present invention is a simple instrument for closing trocar incision sites and delivering sutures. The present invention is a needle assembly in which the needle is constructed of a spring-like material and initially housed within a sheath in a deformed condition. The needle can be easily exposed by sliding an actuator so as to release constraining means and allow the needle to assume its undeformed condition. The needle assembly has few parts, allows a wide range for deflection of the needle, and the needle may be exposed with a relatively short stroke.

A first aspect of the invention comprises a surgical device for suturing a wound in the tissue of a patient comprising:
   a sheath having a longitudinal axis including a proximal end and a distal end;
   a recess formed in the wall of the sheath toward the distal end;
   a needle constructed of a spring-like material, the needle being movable from a first retracted position wherein the needle is withdrawn into the recess to a second exposed position wherein the needle is extended from the recess;
   means for constraining the needle in its retracted position by deforming the needle;
   an actuator at the proximal end of said sheath for releasing the constraining means, so as to thereby allow the needle to assume its undeformed condition and move to the exposed position;
   the needle having a configuration such that upon extension from the distal end of the sheath, the needle points in the direction of the proximal end.

A further aspect of the invention comprises a surgical device for suturing a wound in the tissue of a patient comprising:
   a sheath having a longitudinal axis including a proximal end and a distal end;
   a recess formed in the wall of the sheath toward the distal end;
   a needle constructed of a shape memory alloy material comprising a generally S-shape and including a body having one end fixedly attached to the interior of the distal end of the sheath, the body of the needle being movable in the sheath from a first position wherein the needle is retracted into the recess to a second position exposed wherein the needle is extended laterally from the recess:
   means for constraining the needle in the first position therefor;
   an actuator at the proximal end of the sheath for releasing the constraining means, the actuator comprising:
      a sleeve slidable within the sheath;
      an opening formed in the distal end of the sleeve through which the needle extends in the exposed position;
      wherein the means for constraining comprises a section of the sleeve formed between the opening and the distal end of the actuator such that upon release of the means for constraining the needle moves to the second, exposed position;
   the needle having a configuration such that upon extension from the distal end of the sheath, the needle points in the direction of the proximal end.

DETAILED DESCRIPTION OF THE PREFERRED EMBODIMENT

Figure 1:
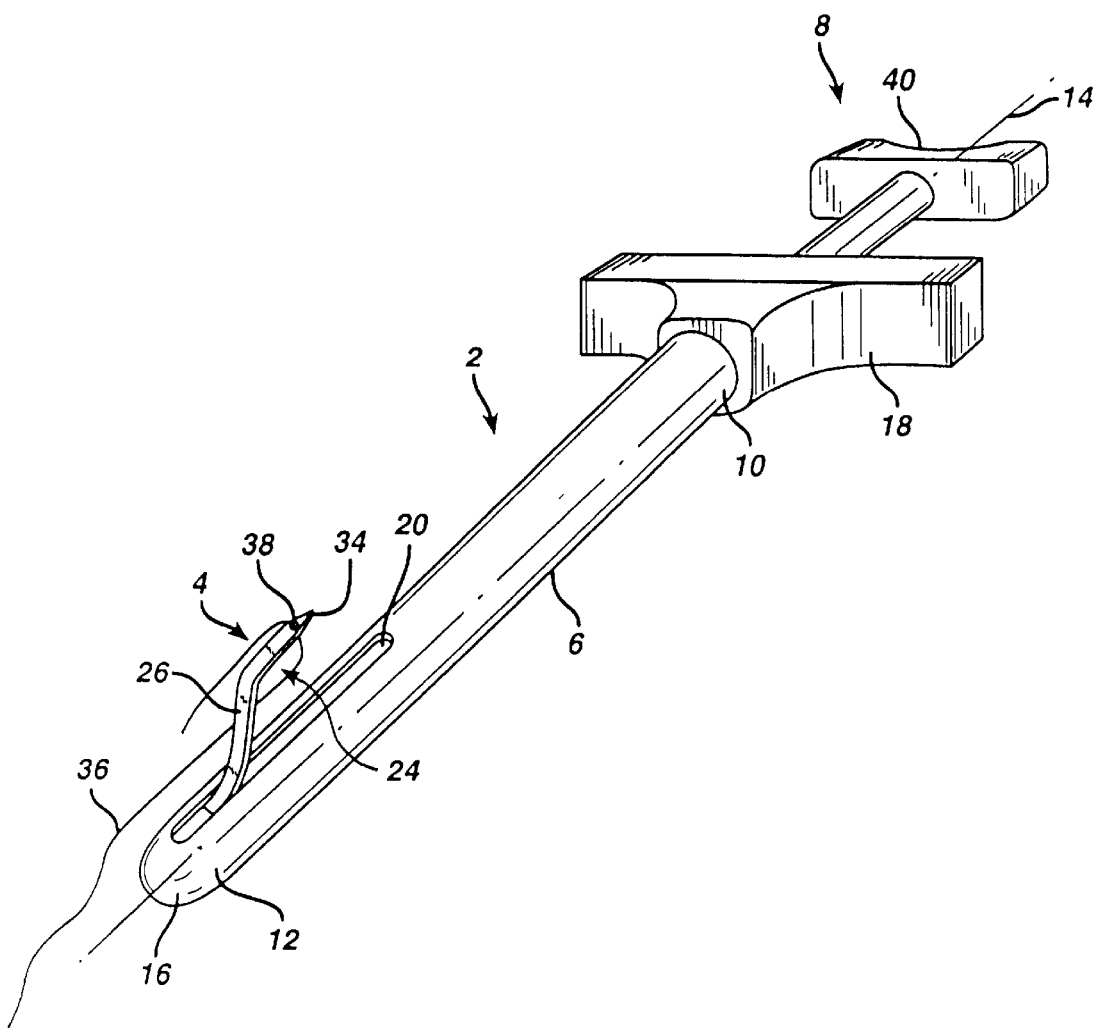
FIG. 1 is a perspective view of the present invention.
Figure 3A:
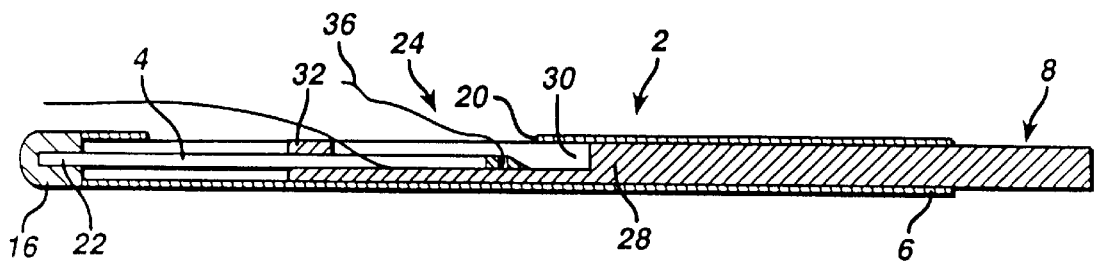
FIGS. 3a, 3b and 3c are schematic views of deployment of the present invention.

Referring now to the drawings, FIG. 1 illustrates a surgical device in the form of a puncture closure device 2 including a needle 4 movable in sheath 6. An actuator 8 is capable of moving needle 4 from a first, retracted position, as seen in FIG. 3a, to a second, exposed position, as seen in FIGS. 1 and 3c. Device 2 is designed to be used in a sterile surgical field. The device may be disposable or reusable or partially disposable or reusable. The outer radial dimension of device 2 is 10 mm or less.

Sheath 6 is a tubular sheath having a proximal end 10 and a distal end 12 disposed along opposite ends of longitudinal axis 14. Sheath 6 includes a blunt tip 16 located at the distal end and a gripping section 18 located at the proximal end. The advantage of a blunt end is to eliminate risk of inadvertent puncture of organs or tissue when inserting the device into a wound. A recess 20 is formed in the wall of the sheath adjacent to blunt tip 16 through which needle 4 may be extended, as seen in the Figures and as discussed below.

Needle 4 includes a body having a generally S-shaped configuration. A first end 22 of needle 4 is fixedly attached to the interior of the distal end of the sheath. Needle 4 may be fixedly attached to sheath 6 at end 22 by pins or other mechanical attachment, or may be formed with the sheath. The end opposite first end 22 of needle 4 is manipulation end 24, which includes a straightened portion 26. It should be noted, however, that the manipulation end may include a curved portion, rather than straightened portion 26. Needle 4 is constructed of a spring-like material. In its undeformed configuration, needle 4 assumes its S-shaped configuration exposed so that the S-shape extends from fixed end 22 through recess 20 to manipulation end 24. Straightened portion 26 is then generally parallel to longitudinal axis 14. In its deformed configuration, the needle is confined within recess 20. Needle 4 moves from its retracted position to its exposed position by operation of actuator B. When manipulation end 24 is retracted within recess 20, puncture closure device 2 is in its retracted position. When the manipulation end is extended from recess 20, the puncture closure device is in the exposed position.

As discussed above, needle 4 may be constructed of a spring-like material, such as a shape memory alloy or stainless steel. The requirements are that the material be sufficiently resilient and bio-compatible. However, the needle is preferably constructed of a shape memory alloy, more preferably of superelastic material, and most preferably of an alloy including nickel titanium. With shape memory alloys, the radius of curvature of the S-shape can be smaller than with conventional materials, thereby permitting construction of a needle which has a configuration in which the manipulation end of the needle may be a greater distance from the sheath and in which the length of the S-shaped needle may be shorter.

Actuator 8 includes a sleeve 28 slidable within sheath 6. The proximal portion of the sleeve may be solid or rod-like, or may be substantially hollow. Sleeve 28 Includes an opening 30 formed adjacent to the distal end of the sleeve, leaving a section of sleeve 32 between the distal tip of the sleeve and its opening 30. Section 32 forms a ring-shaped portion encircling needle 4 which extends from distal end 12 of the sheath, through the distal tip of the sleeve. In its initial state, section 32 is positioned on manipulation end 24 so as to deform needle 4, thereby constraining the needle in recess 20 in its retracted position. As actuator 8 is deployed, sleeve 28 slides toward the distal end of sheath 6, releasing the needle from section 32 and allowing needle 4 to assume its undeformed S-shaped configuration, thereby exposing the needle for use. In this position, manipulation end 24 extends through opening 30, as well as through recess 20. Device 2 may be returned to its initial state by sliding actuator 8 within sheath 6. With an actuation arrangement as described in the present invention, the device can be actuated with a short longitudinal stroke. A stop having cooperating surfaces on actuator 8 and sheath 6 prevents the actuator from being accidentally withdrawn completely from the sheath.

Manipulation end 24 of needle 4 terminates in a sharp point 34. Manipulation end 24 includes means for slidably receiving and retaining a suture 36. The means for slidably receiving and retaining suture 36 may be in the form of a hole 38, as seen in the FIGS. or a notch, not shown. The hole or notch is sized to accommodate sutures of varying diameters. In any of these embodiments, sharp point 34 is capable of piercing the tissue adjacent to the patient's wound when extended by actuator 8.

A thumb grip 40 is disposed at the proximal end of sleeve 8 for actuating in conjunction with gripping sections 18 of sheath 6.

Figure 3B:
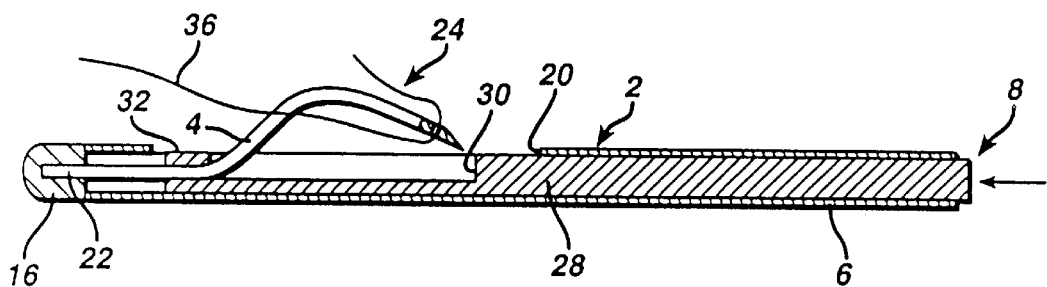
Figure 3C:
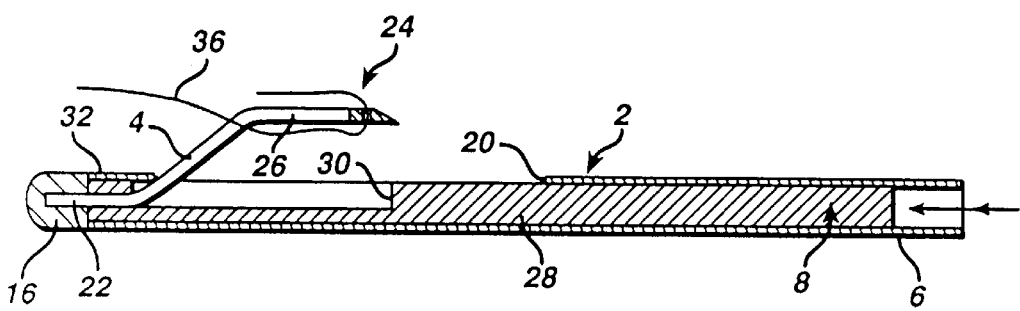

In operation, puncture closure device 2 is introduced into a wound with suture 36 attached, as shown in FIG. 3, by threading suture 36 through hole 38 or notch) located in the manipulation end of the needle. Device 2 is positioned within the wound such that sharp point 34 is beneath the tissue to be sutured. Actuator 8 is then deployed by holding two fingers beneath gripping section 18 and using thumb grip 40 to push the gripping section and thumb grip relative to each other, so as to move needle 4 from a first position retracted within sheath 6, as seen in FIG. 3a, through an intermediate position as shown in FIG. 3b, to the exposed position as shown in FIG. 3c. However, it is to be understood that any gripping means could be employed for actuating the device, such as pistol grip, scissors action screw mechanism or plunger mechanism. At this point, sharp point 34 points in the proximal direction, toward actuator 8. Device 2 is pulled upward, through tissue, from the internal layers to the external layers, driving sharp point 34 of needle 4 and suture 36 through one edge of the tissue surrounding the wound. A first portion of suture 36 is pulled through the tissue. The device may be temporarily returned to the intermediate position shown in FIG. 3b to facilitate suture retrieval from the wound edge. Device 2 is then pushed back through the tissue in the direction from external tissue to internal tissue, such that the needle is no longer piercing any tissue. Suture 36 is still attached to needle 4. Device 2 is rotated within the wound. The device is again pulled upward, through the opposite edge of tissue, from internal layers to external layers, such that the other tissue edge of the wound is pierced with the sharp point of the needle, pulling the other end of suture 36 through the tissue. The device may be again temporarily returned to its intermediate position as seen in FIG. 3b. Suture 36 is removed from the needle, such that suture 36 is now completely free from device 2. Needle 4 is pushed back through the pierced tissue in the direction from external tissue to internal tissue, fully through the internal layer so that the sharp point of the needle is not piercing any tissue. Needle 4 may be returned to its retracted position such that section 32 of sleeve constrains the needle. Device 2 is fully withdrawn from the wound. Suture 34 is tied. The specific positions of FIGS. 3a, 3b and 3c may be determined by any suitable means, for example a detent between the sheath and the sleeve.

Figure 2:
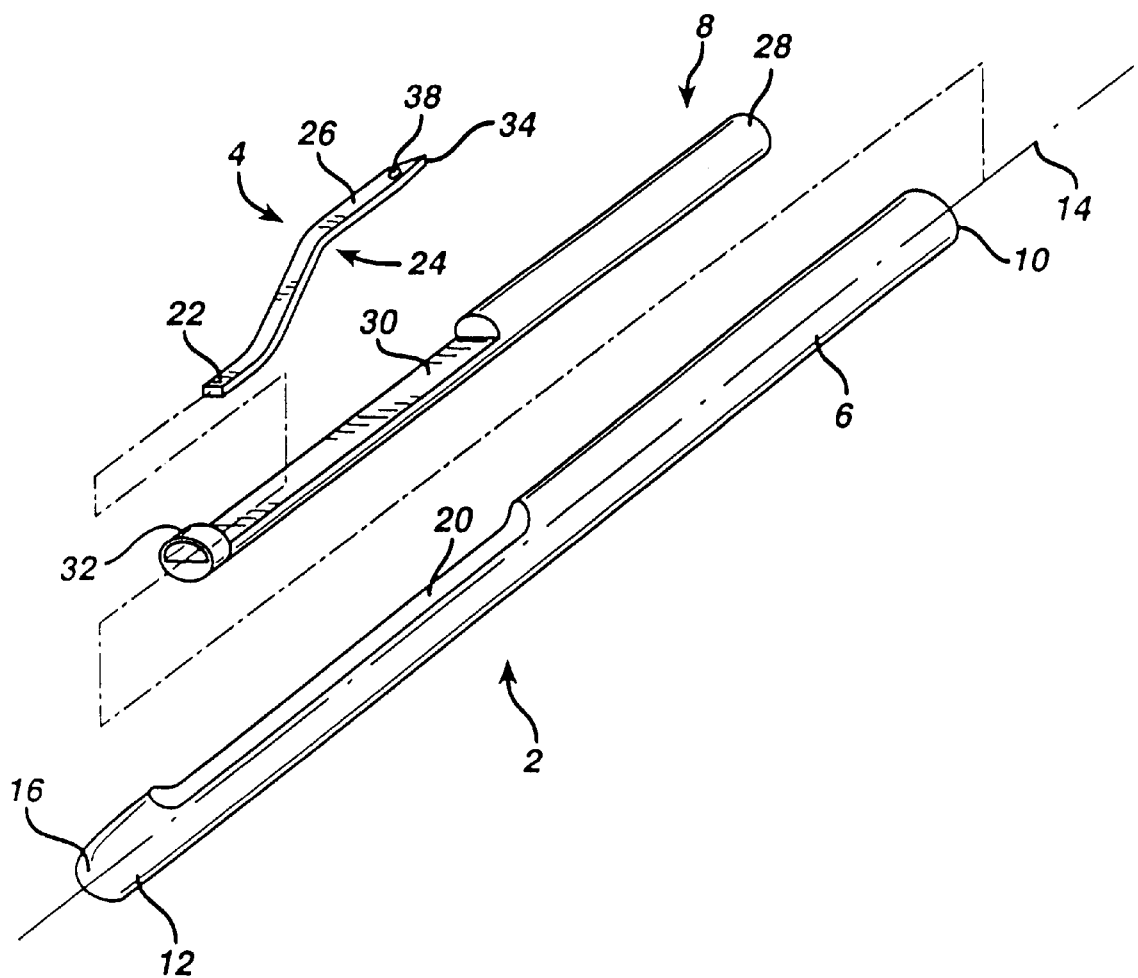
FIG. 2 is an exploded view of the device of FIG. 1.
Figure 4A:
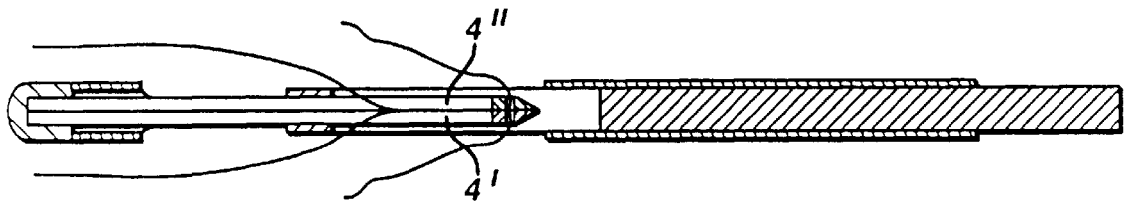
FIGS. 4a, 4b and 4c are schematic views of a second embodiment of the present invention.
Figure 4B:
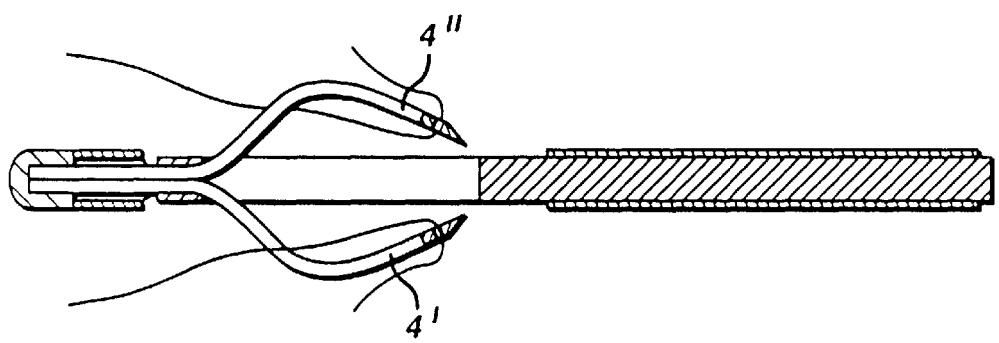
Figure 4C:
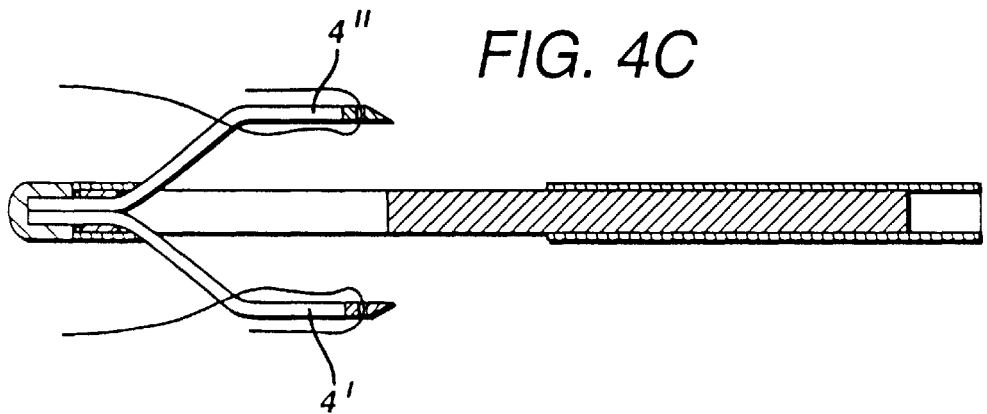

Device 2 may be constructed with double needles, as shown in FIGS. 4a–4c. FIG. 4a illustrates double needles 4', 4" in the retracted position, moving through an intermediate position shown in FIG. 4b to FIG. 4c, which illustrates needles 4', 4' in the exposed position. Actuation of the device may be achieved by a single actuator as described above, or with the use of dual sleeves. Operation of the device is generally the same as that described in connection with the embodiment of FIGS. 1–3.

While the needle is described as being fixed to the sheath, it is within the scope of this invention to construct the device with the needle fixed to the distal end of the actuator, rather than the sheath. Variations and modifications can be made to the present invention without departing from the scope of the present invention, which is limited only by the following claims.

I claim:

1. A method of suturing a wound, comprising:
    (a) providing a surgical device comprising:
        i) a housing including a proximal end, a distal end, a wall defining a chamber, and an opening formed in the wall at the distal end, in communication with the chamber;

ii) a needle comprised of a resilient material which transforms from an undeformed configuration to a deformed configuration upon the application of stress to the needle, the needle being in the deformed configuration in the chamber and the needle reversibly transforms to the undeformed configuration and extends exteriorly of the chamber through the opening upon release of the stress from the needle, the needle having a fixed end non-movably attached to the interior of the distal end of the housing; and (b) attaching a suture to the needle;

(c) inserting the surgical device into the wound with the needle in the deformed configuration;

(d) releasing the stress from the needle to transform the needle from the deformed configuration to the undeformed configuration such that the needle extends exteriorly of the housing through the opening in the wall and such that the needle extends exteriorly at a point proximal to the distal end of the housing, the needle having an attached suture;

(e) suturing the wound using the surgical device; and, (f) withdrawing the surgical device from the wound.

2. The method as defined in claim 1 further comprising before the step of withdrawing, the step of applying stress to the needle to transform the needle from the undeformed configuration to the deformed configuration and to withdraw the needle through the opening and into the chamber.

3. The method of claim 1 wherein the needle is comprised of a superelastic material which is superelastically deformed by application of stress to the needle.

4. A method of suturing a wound, comprising:

(a) providing a surgical device including:
   i) a housing including a proximal end, a distal end, a wall defining a chamber, and a pair of openings formed in the wall at the distal end, in communication with the chamber; and
   ii) a pair of needles each comprised of a resilient material which reversibly transforms from an undeformed configuration to a deformed configuration upon the application of stress to the needle, the needles each being in the deformed configuration in the chamber and the needles each transforming to the undeformed configuration and extending exteriorly of the chamber through one of the openings upon release of the stress from the needles, the needles each having a fixed end non-movably attached to the interior of the distal end of the housing;

(b) inserting the surgical device into the wound with the needles in the deformed configuration;

(c) releasing the stress from the needles to transform the needles from the deformed configuration to the undeformed configuration such that the needles extend exteriorly of the housing each through one of the openings in the wall and such that the needles extend exteriorly each at a point proximal to the distal end of the housing, the needles each having an attached suture;

(d) suturing the wound; and, (e) withdrawing the surgical device from the wound.

5. The method as defined in claim 4 further comprising before the step of withdrawing, the step of applying stress to the needles to transform the needles from the undeformed configuration to the deformed configuration and to withdraw the needles each through one of the openings and into the chamber.

6. The method of claim 4 wherein the needles are comprised of a superelastic material which superelastically deforms upon application of the stress to the needles.

7. A method of suturing a wound, comprising:

(a) providing a surgical device including:
   i) a housing including a wall defining a chamber and an opening in communication with the chamber;
   ii) a needle comprising a first end and a second end and comprised of a shape memory material which reversibly transforms from an undeformed configuration to a deformed configuration upon the application of stress to the needle; and
   iii) a sheath comprising a distal end, a proximal end, an interior portion and an exterior portion wherein the first end of the needle is attached to the interior portion of the sheath at the distal end of the sheath;
   iv) a slidable sleeve contained within the sheath wherein the sleeve slides within the sheath to releasably apply stress to the needle so as to transform the needle between the deformed configuration and the undeformed configuration;

(b) inserting the surgical device into the wound with the needle in the deformed configuration;

(c) releasing the stress from the needle to transform the needle from the deformed configuration to the undeformed configuration such that the needle extends exteriorly of the housing through the opening in the wall and such that the needle extends exteriorly at a point proximal to a distal end of the housing, the needle having an attached suture;

(d) suturing the wound; and (e) withdrawing the surgical device from the wound.

8. The method as defined in claim 7 further comprising before the step of withdrawing, the step of applying stress to the needle to transform the needle from the undeformed configuration to the deformed configuration.

9. The method of claim 7, wherein the needle is deployed in its undeformed configuration aided by body temperature at the interior of the wound.

10. A method of suturing a wound in the tissue of a patient, the method comprising:

(a) providing a needle comprised of a superelastic material;

(b) applying a physical stress to the needle to place the needle in a deformed configuration;

(c) inserting the needle into the wound in the abdominal wall in the deformed configuration;

(d) releasing the stress from the needle to transform the needle from the deformed configuration to the undeformed configuration, the needle having an attached suture;

(e) suturing the wound; and (f) withdrawing the needle from the wound.

11. The method as defined in claim 10 further comprising before the step of withdrawing, the step of applying stress to the needle to transform the needle from the undeformed configuration to the deformed configuration.

12. The method of claim 10 wherein the wound in the abdominal wall is created by a trocar.

13. The method of claim 10, wherein the needle is deployed in its undeformed configuration aided by body temperature at the interior of the wound.

14. A method of suturing a wound comprising the steps of:

(a) providing a surgical device comprising:
   i) a sheath having a longitudinal axis including a proximal end and a distal end;

ii) a recess formed in the wall of the sheath toward the distal end;

iii) a needle constructed of a spring-like material, the needle having a fixed end non-movably attached to the interior of the distal end of the sheath, and the needle being movable from a first retracted position wherein the needle is withdrawn into the recess to a second generally undeformed exposed position wherein the needle is extended from the recess, the needle having a configuration such that upon extension from the distal end of the sheath, the needle points generally in the direction of the proximal end;

iv) a restraining mechanism for constraining the needle in the first retracted position by elastically deforming the needle;

v) an actuator at the proximal end of the sheath for releasing the restraining mechanism, so as to thereby allow the needle to assume an undeformed condition and move to the second exposed position;

(b) inserting the surgical device into the wound with the needle in the deformed configuration;

(c) releasing the stress from the needle to transform the needle from the deformed configuration to the undeformed configuration;

(d) suturing the wound; and, (e) removing the surgical device from the wound.

* * * * *